US00PP11665P

United States Patent [19]

van Andel

[11] Patent Number: Plant 11,665

[45] Date of Patent: Dec. 5, 2000

[54] ALSTROEMERIA PLANT NAMED 'STADICREM'

[75] Inventor: Jacob van Andel, Aalsmeer, Netherlands

[73] Assignee: Van Staaveren B.V., Aalsmeer, Netherlands

[21] Appl. No.: 09/226,318

[22] Filed: Jan. 6, 1999

[51] Int. Cl.[7] ..... A01H 5/00

[52] U.S. Cl. ..... Plt./309

[58] Field of Search ..... Plt./309

[56] References Cited

U.S. PATENT DOCUMENTS

P.P. 9,100 4/1995 van Andel ..... Plt./309

*Primary Examiner*—Howard J. Locker

*Attorney, Agent, or Firm*—Christie, Parker & Hale, LLP

[57] ABSTRACT

A new and distinct Alstroemeria plant variety producing flowers of good quality and attractive coloration.

1 Drawing Sheet

BACKGROUND OF THE INVENTION

The present invention relates to a new and distinct variety of Alstroemeria which was discovered as a whole plant mutation of unknown causation of the variety known as 'Stamond' (U.S. Plant Pat. No. 9,100) in Aalsmeer, The Netherlands. The varietal denomination of the new variety is 'Stadicrem'.

The first act of asexual reproduction of 'Stadicrem' was in Aalsmeer, The Netherlands, by propagation by dividing the rhizomes. Asexual reproduction by dividing rhizomes through successive generations in Aalsmeer, The Netherlands, has demonstrated that the combination of characteristics as herein disclosed for 'Stadicrem' are firmly fixed and retained through successive generations.

COMPARISON WITH PARENT

The new variety differs from the parent in flower color.

SUMMARY OF THE INVENTION

The new variety of Alstroemeria, 'Stadicrem', produces large pale yellow flowers.

DESCRIPTION OF ILLUSTRATION

The new variety of Alstroemeria hybrid is illustrated in the accompanying illustration, which shows typical flower characteristics, with colors being as nearly true as is possible for illustrations of this type.

DETAILED DESCRIPTION OF THE NEW VARIETY

The following is a detailed description of the new cultivar of Alstroemeria hybrid as observed in a greenhouse in Aalsmeer, The Netherlands. Color designations indicated are in accordance with The Royal Horticultural Society Colour Chart by color plate designations.

'Stadicrem' has not been observed under all possible environmental conditions. Phenotypic expression may vary with variations in environment such as temperature, light intensity, day length and growing and cultural conditions.

Botanical classification:

*Family.*—Amaryllidaceae.

*Genus.*—Alstroemeria sp.

Plant:

*Form.*—Bush.

*Shape.*—Upright.

*Height.*—About 150–250 cm.

*Main stem.*—About 200 cm.

*Internode length.*—About 1–8 cm.

*Growth.*—Vigorous.

*Strength.*—Strong.

*Rhizomes.*—Plant about 1 to 2 years old. Color: Near 155D. Size: About 10 to 30 cm.

Foliage:

*Quantity.*—Abundant.

*Number of leaves.*—About 35 to 45 per stem.

*Size of leaf.*—Length: About 15 to 20 cm. Width: About 3 to 5 cm.

*Shape of leaf.*—Elliptical.

*Margin.*—Straight, entire.

*Texture.*—Glossy.

*Color.*—Upper side: Near 137A. Underside: Near 137C.

Flower:

*Blooming habit.*—Continuous, blooms profusely, throughout the year.

*Size when first anthers release their pollen.*—Diameter: About 7 cm. Depth: About 5 cm.

*Borne.*—About 4 to 5 flowers per umbel.

*Shape or form.*—When bloom first opens: Cup. When bloom matures: Cup.

*Fragrance.*—None.

*Lasting quality.*—On plant: About 4 weeks. As cut flower: About 18 to 20 days.

Tepalage:

*Number of tepals.*—About 6.

*Arrangement.*—About 2 concentric circles of about 3 tepals.

*Form.*—Obovate.

*Margin.*—Minutely crimped.

*Apex.*—Pointed.

*Lastingness of bloom.*—About 4 weeks.

*Texture.*—Soft.

*Appearance.*—Velvety; inner tepals and outer tepals are obovate.

*Color.*—Outer tepals: Body near 2D; base near 2D; underside near 2D/36D; about 0–5 spots, near 185A. Inner tepals: Body near 2D; base near 2D; underside near 2D; about 20–40 spots, near 185A; inner median tepal about 0–15 spots, color near 185A general coloration predominantly white with some pale yellow toward inner papillated portion of inner tepals. General: Difference between inner lateral tepals and inner median tepal is the number of spots.

Flower stem:

*Length.*—About 5 to 8 cm.

*Color.*—Near 137B.

*Strength.*—Strong, erect.

*Persistence.*—Flower does not hang on and dry.

*Disease resistance.*—Unknown.

Bud:

*Size.*—Diameter: About 1 to 2 cm. Depth or length: About 2 to 4 cm.

*Form.*—Pear-shaped.

*Rate of opening.*—Fast.

*Color of tepals when tepals first divide.*—Near 2D and 138A.

*Color of tepals when tepals begin to unfurl.*—Near 2D and 138A.

Reproductive organs:

*Stamen.*—Number: About 6. Arrangement: Side by side around the style.

*Anthers.*—Size: About 8 to 10 mm. Color: Near 161A.

*Filaments.*—Length: 5 cm. Color: Near 2D.

*Pollen.*—Color: Near 164A.

*Pistils.*—1. Styles: Length about 4 to 5 cm. Color: Near 2D.

*Stigmas.*—Color: Near 2D.

Fruit: Fertile.

*Shape.*—Round.

*Color at maturity.*—Near 163A.

I claim:

1. A new and distinct Alstroemeria plant of the variety substantially as shown and described.

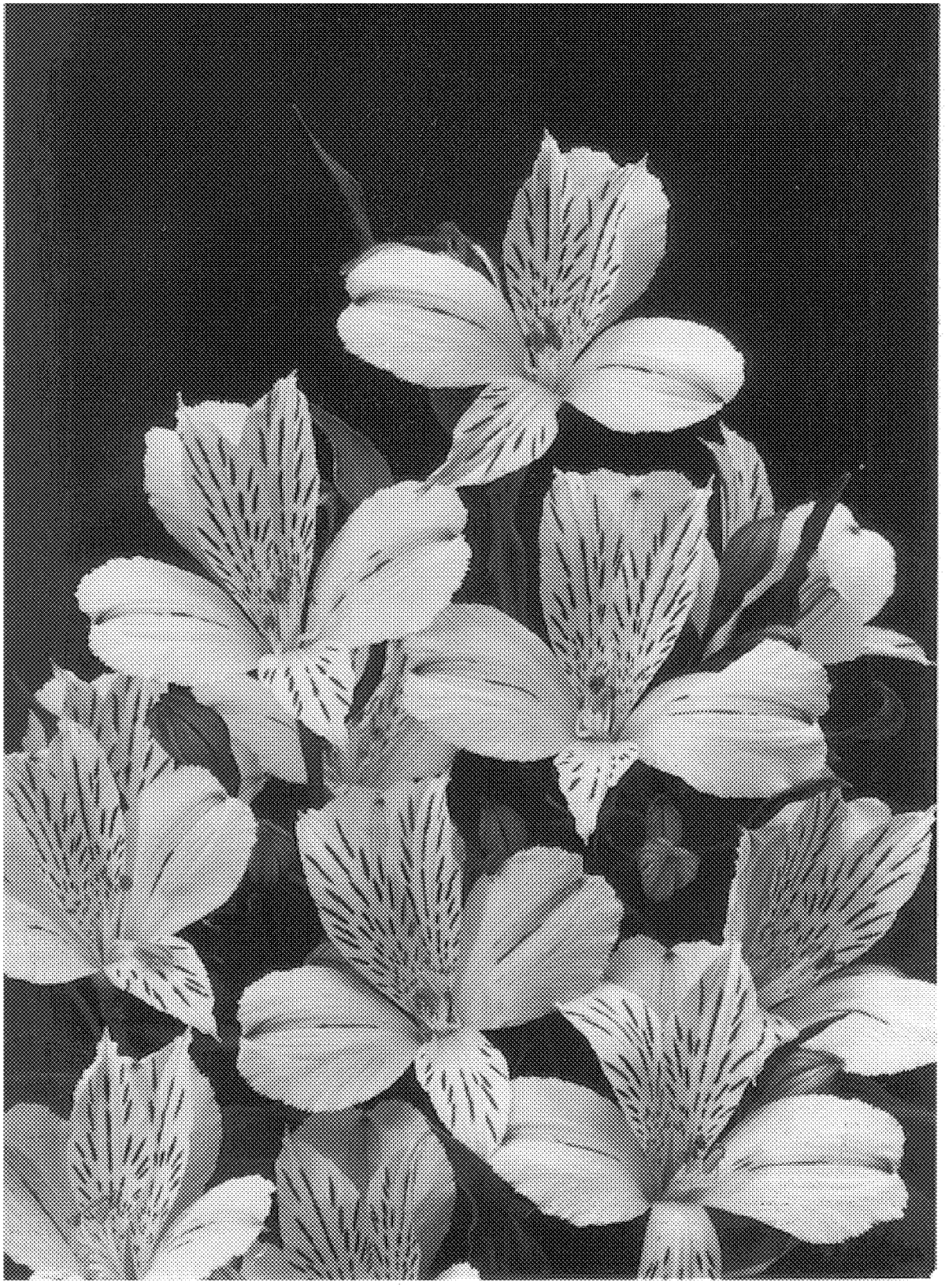

* * * * *